United States Patent
Kettel et al.

(10) Patent No.: US 11,937,922 B2
(45) Date of Patent: *Mar. 26, 2024

(54) pH-TRIGGERED DIAGNOSTIC WOUND DRESSING

(71) Applicant: PAUL HARTMANN AG, Heidenheim (DE)

(72) Inventors: Markus Kettel, Heidenheim (DE); Andrew Tobias Jenkins, Bath (GB); Laura Wallace, Bath (GB)

(73) Assignee: PAUL HARTMANN AG, Heidenheim (DE)

(*) Notice: Subject to any disclaimer, the term of this patent is extended or adjusted under 35 U.S.C. 154(b) by 362 days.

This patent is subject to a terminal disclaimer.

(21) Appl. No.: 17/288,380

(22) PCT Filed: Oct. 23, 2019

(86) PCT No.: PCT/EP2019/078949
§ 371 (c)(1),
(2) Date: Apr. 23, 2021

(87) PCT Pub. No.: WO2020/084017
PCT Pub. Date: Apr. 30, 2020

(65) Prior Publication Data
US 2021/0378565 A1     Dec. 9, 2021

(30) Foreign Application Priority Data

Oct. 24, 2018  (EP) ..................................... 18202424

(51) Int. Cl.
| | | |
|---|---|---|
| *A61B 5/145* | (2006.01) | |
| *A61B 5/00* | (2006.01) | |
| *A61K 49/00* | (2006.01) | |
| *A61L 26/00* | (2006.01) | |

(52) U.S. Cl.
CPC ........ *A61B 5/14539* (2013.01); *A61B 5/6802* (2013.01); *A61K 49/0069* (2013.01); *A61L 26/0019* (2013.01); *A61L 26/008* (2013.01)

(58) Field of Classification Search
CPC ................................................ A61K 49/0069
See application file for complete search history.

(56) References Cited

U.S. PATENT DOCUMENTS

| | | |
|---|---|---|
| 2004/0241214 A1 | 12/2004 | Kirkwood et al. |
| 2013/0064772 A1 | 3/2013 | Swiss et al. |
| 2013/0204217 A1 | 8/2013 | Junginger et al. |
| 2016/0262672 A1 | 9/2016 | Hammond et al. |
| 2019/0076631 A1* | 3/2019 | McHugh .............. A61K 9/0024 |
| 2021/0379241 A1* | 12/2021 | Kettel .................... A61L 15/42 |

FOREIGN PATENT DOCUMENTS

| | | |
|---|---|---|
| CN | 105592834 | 5/2016 |
| WO | WO 2002/47737 | 6/2002 |
| WO | WO 2003/026544 | 4/2003 |
| WO | WO 2013/036771 | 1/2013 |
| WO | WO 2013/104876 | 7/2013 |
| WO | WO 2017/173069 | 10/2017 |

OTHER PUBLICATIONS

Chinese Office Action dated Dec. 15, 2021, in corresponding CN Patent Application No. 2019/80069902.
Chinese Search Report dated Dec. 3, 2021, in corresponding CN Patent Application No. 2019/80069902.
European Search Report and Written Opinion, dated May 21, 2019, in corresponding EP Patent Application No. 18202424.0.
International Search Report and Written Opinion, dated Feb. 10, 2020, corresponding to International Application No. PCT/EP2019/078949, (from which the present application claims priority,) 3 pp.
Shula et al. (2007) "Evaluation of pH measurement as a method of wound assessment," J. Wound Care; 16(7), pp. 291-294.
Thet et al. (2016) "Prototype Development of the Intelligent Hydrogel Wound Dressing and Its Efficacy in the Detection of Model Pathogenetic Wound Biofilms," ACS Appl. Mater Interfaces, 8 (24) pp. 14909-14919.

* cited by examiner

*Primary Examiner* — Gina C Justice
(74) *Attorney, Agent, or Firm* — Leydig, Voit & Mayer, Ltd.

(57) ABSTRACT

The invention relates to a functional wound dressing being able to detect and indicate the state of the wound, in particular with regard to an infection which is reported to be frequently associated with poorly healing wounds, such as chronic wounds. The present wound dressing can be used in moist wound healing and contains a substance being able to absorb wound exudate from the wound and to provide moisture to the wound.

15 Claims, 2 Drawing Sheets pH-TRIGGERED DIAGNOSTIC WOUND DRESSING

CROSS-REFERENCE TO RELATED APPLICATIONS

This application is a U.S. National Stage Application filed under 35 U.S.C. §371 of International Application No. PCT/EP2019/078949, filed Oct. 23, 2019, which claims the benefit of EP Application No. 18202424.0, filed Oct. 24, 2018. Both of these applications are hereby incorporated by reference in their entireties.

The invention relates to a functional wound dressing being able to detect and indicate the state of the wound, in particular with regard to an infection which is reported to be frequently associated with poorly healing wounds, such as chronic wounds. The present wound dressing can be used in moist wound healing and contains a substance being able to absorb wound exudate from the wound and to provide moisture to the wound.

A wound can be regarded as separation of the contiguity of tissues of the skin, wherein this can be combined with a loss of substance.

The healing of wounds is based on the ability of the skin to regenerate tissue such as epithelial tissue, connective and supporting tissue. The regeneration of tissue is a complex occurrence of cell activities overlapping with each other, wherein said cell activities promote the healing process step by step. An accumulation of wound exudate, which might contain inter alia blood, proteins, residues of cells, microorganisms and leucocytes, can promote the growth of bacteria.

It is reported that, like any chemical reaction, the metabolism during wound healing is dependent on optimum pH values and wound pH is considered as an important role in therapeutic interventions in wound healing. The pH of the wound inter alia affects the following processes during wound healing, such as oxygen release, angiogenesis, protease activity and bacterial toxicity. With reference to Shula V K, et al.: "Evaluation of pH measurement as a method of wound assessment", J. Wound Care, 2007; 16(7), pp. 291-294, a slightly acidic pH value of about 5.5 corresponding to the pH value of the outer surface of the skin is considered to promote oxygen perfusion, decreased bacteria presence, decreased proteolytic activity from proteases and enhanced fibroblast growth.

Wounded skin exposed to underlying hypodermis with a pH substantially equivalent to the internal pH of the body (7.0 to 9.0) and bacteria waste products, such as ammonia or toxins, can contribute to the elevation of the pH level of the wound to alkaline levels. Poorly or non-healing wounds, such as for example chronic wounds, have an elevated alkaline wound milieu with a pH being recorded in the range of 7.1 to 8.2.

Keeping the above in mind and in order to improve the wound healing by appropriate handling or treatment, the state of the wound with regard to the grade of infections should be detected, the earlier the better.

WO 2017/173069 A1 relates to microbial infection indicator devices including a dressing with indicators, stand-alone indicator inserts or disks that can be freely placed at a wound site or dressing and applications thereof for displaying a visible or detectable signal to a user upon detection of an analyte or biomarker indicative of an infection, such as a colour change.

WO 03/026544 A1 relates to a wound dressing comprising a wound contacting sheet having a wound-facing surface and a back surface opposite the wound-facing surface and having apertures therein that open or enlarge in the presence of wound exudate and a plurality of particles comprising one or more therapeutic agents located behind the back surface of the back sheet, wherein the particles are able to pass through the apertures to the wound-facing surface of the sheet when the apertures are opened or enlarged in the presence of said wound exudate.

WO 2013/03771 A1 relates to topical, pH-sensitive compositions which comprise an antibiotic or an antibiotic and a pH indicator and devices comprising such compositions. The pH-sensitive compositions are described to be substantially stable under basic and neutral pH, such as normal physiological pH, but to degrade under acidic pH (formation of $CO_2$) so as to release the antibiotic contained therein, i.e. the antibiotic release is triggered by the microorganism's production of $CO_2$ at the wound site, which forms carbonic acid and lowers the pH, and thus results in the rupture of the pH-sensitive component.

WO 2013/104876 as well as Thet N. T. et al: "Prototype Development of the Intelligent Hydrogel Wound Dressing and Its Efficacy in the Detection of Model Pathogenetic Wound Biofilms", ACS Appl. Mater Interfaces, 2016, 8 (24) pages 14909-14919, describe the use of lipid vesicles. Said lipid vesicles contain a fluorescent dye which is released from the vesicle at contact with toxins produced for example by bacteria such as *S. aureus* and/or *P. aeruginosa*, wherein the released dye can be detected by its fluorescence. Further, said documents describe a wound dressing using the lipid vesicles in a matrix of agarose gel. Agarose is a polysaccharide made up of the repeating unit of agarobiose, which is a disaccharide of D-galactose and 3,6-anhydro-L-galactopyranose. Agarose gel is reported to be present in an almost completely hydrated form (99%), which allows to provide water to the wound and, thus, to keep the wound humid. In turn, agarose gel seems to be improvable as far as the uptake of fluids from the wound, such as exudate, is concerned. Further, the wound dressing described in the above-mentioned documents has a milky-cloudy appearance and, thus, seems to be improvable with regard to the transparency. Transparency would allow an easy visual inspection of the fluorescence and, thus, an indication of the presence of bacteria and/or the state of the wound healing.

Hence, it was an object of the present invention to overcome the above drawbacks.

Thus, there is still a need for wound dressings capable of keeping the wound humid but simultaneously adsorbing liquid, such as exudate from the wound, wherein the wound dressing further allows an easy visual inspection of the condition of the wound.

In particular it was an object of the present invention to provide a wound dressing with humidity-modulating properties. Especially, the wound dressing should not only provide humidity to the wound to keep it moist, but also adsorb (remove) exudate produced in the wound inhibiting the healing process. Further, the wound dressing should allow an easy visual detection of the state of a wound, i.e. whether the wound healing is proceeding as desired or whether the healing process fails or comes to a standstill for example caused by an infection. With regard thereto, it should be assured that the release of the indicator (fluorescent) is triggered by compounds of a poorly-healing, infected wound and not by compounds of the wound dressing itself. Moreover, the wound dressing should maintain its integrity under common sterilization conditions such as conditions under which sterilization via radiation is carried out. Further, the indicator should substantially be prevented from reaching the wound site and having direct contact to the wound.

SUMMARY

The present invention has unexpectedly solved the above objectives by a new wound dressing comprising a hydrogel layer, a layer comprising a pH-sensitive polymer and one or more compartments comprising a carrier containing fluorescent dye, wherein the one or more compartment(s) are specially arranged in or on the layer comprising a pH-sensitive polymer.

Thus, the subject of the present invention is a wound dressing comprising
a) a hydrogel layer facing towards the wound,
b) a layer comprising a pH-sensitive polymer, and
c) one or more compartment(s) comprising carrier containing fluorescent dye, wherein each compartments c) is placed in or on layer b).

A further subject of the present invention is a method for preparing a layer comprising a pH-sensitive polymer and one or more compartments comprising carrier containing fluorescent dye, wherein each compartment is embedded in the layer comprising pH-sensitive polymer, wherein the method comprises the steps of
  (i) providing a layer comprising a pH-sensitive polymer and having one or more recess(es),
  (ii) adding a solution comprising precursor carrier and fluorescent dye into the recess(es) of the layer from step (i), and
  (iii) hardening the carrier.

A further subject of the present invention is a method for preparing a wound dressing according to the invention, wherein the method comprises the steps of
  (i) providing layer a) according to the present invention
  (ii) applying layer b) and one or more compartments comprising carrier containing fluorescent dye, wherein each compartment is embedded in layer b) on layer a), wherein the compartment is embedded in the surface of layer b) being opposite to the surface being in contact with layer a)
  (iii) optionally applying a backing layer on the surface of layer b) wherein each compartment is embedded.

Additionally, the subject of the present invention is the use of a compartment comprising carrier containing fluorescent dye, wherein said compartment is placed in or on a pH-sensitive polymer as infection indicator for wounds.

Finally, a subject of the invention is a florescent dye for use in diagnosing an infection in a wound, wherein the fluorescent dye is contained in a carrier comprised by one or more compartments, wherein each compartment is placed in or on a layer comprising a pH-sensitive polymer.

BREIF DESCRIPTION OF THE DRAWINGS

DETAILED DESCRIPTION OF THE INVENTION

Figure 1:
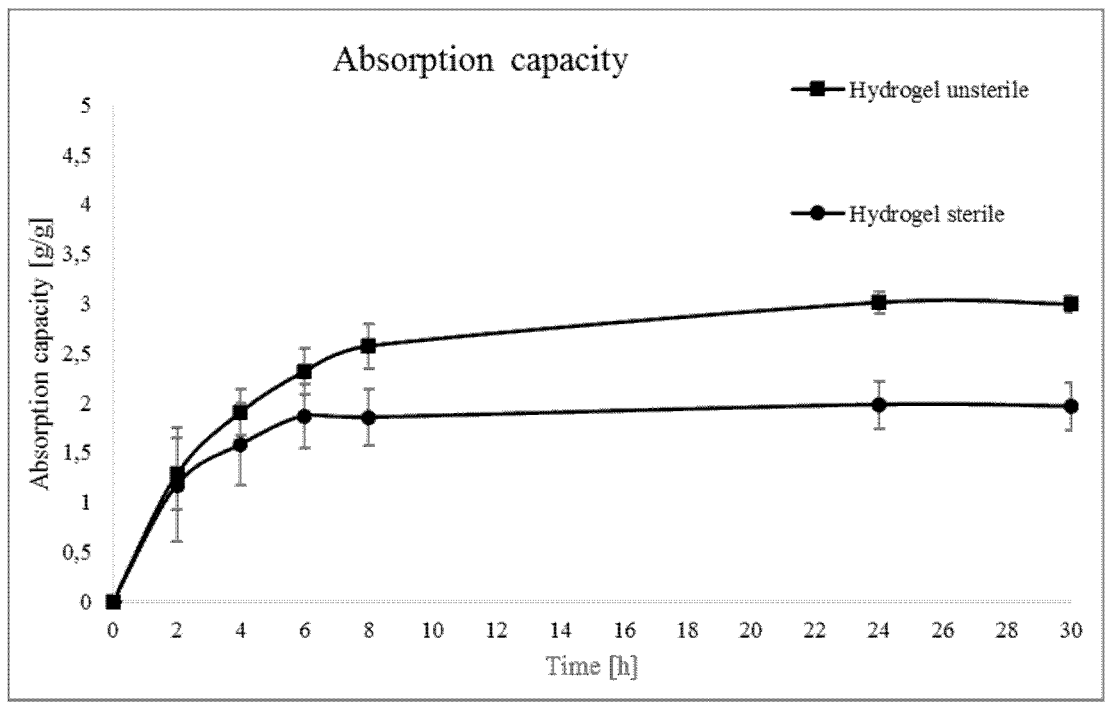
FIG. 1 shows a graph illustrating the adsorption capacity of an obtained hydrogel of the present invention.

Components (a) to (c) of the wound dressing in accordance with the present invention are described in the following.

The present wound dressing comprises a hydrogel layer facing towards the wound. In a preferred embodiment the hydrogel layer facing towards the wound is the wound contact layer, i.e. the hydrogel layer is the outermost layer of the present wound dressing directly contacting the wound site.

In line with the present application a hydrogel is referred to as a synthetic or natural polymeric material, preferably a hydrophilic synthetic or natural polymeric material, which is capable of gel formation within a liquid, preferably water. The synthetic or natural polymeric material can be regarded as a matrix or hydrogel matrix.

The selected hydrogel comprised by the present composition can be preferably based on natural polymeric material selected from starch, dextran, agarose, pectin, alginate, chitosan, hyaluronic acid, gellan, polypeptide and cellulose. Optionally, the natural polymeric material can be further processed, for example by chemical derivation such as the formation of esters and ethers or pharmaceutically acceptable salts.

Starch is a polysaccharide containing a large number of α-D-glucose units which are joined by glycosidic bonds. Starch can be produced by mot plants and used as energy storage. Starch is regarded as insoluble in cold water (23° C.) but is able to exothermically swell up by physically binding a morefold of water compared to its own weight.

Dextran is a complex branched polysaccharide containing glucose units only, wherein the chains have different number average molecular weights from 10.000 to 50.000.000 Daltons determined by gel permeation chromatography. The straight chain consists of glucose molecules being bonded by α-1,6 glycosidic linkages, while branches begin from α-1,3 linkages. Brought into contact with water, dextran forms highly viscous liquids (gels).

Agarose is a polysaccharide having a molecular weight of about 120.00 Daltons which can be obtained by the extraction from certain forms of red seaweed. The chain is linear and made up of repeating agarobiose units, wherein agarobiose in turn is a disaccharide made up of D-galactose and 3,6-anhydro-L-galactopyranose linked by α-(1→3) and β-(1→4) glycosidic bonds. Agarose can be a white solid, preferably a powder, which is able to substantially completely dissolve in water of a temperature of 80 to 100° C. and forms a gel when it cools.

Pectin is a vegetable structural polysaccharide obtainable from plants, such as citrus fruits. Pectin is a polysaccharide (more exactly a polyuronide) which mainly contains D-galacturonic acid units being α-1,6 glycosidicly joined. All, just a part or none of the carboxy residues of the galacturonic acid in pectin can be present in an esterified form, for example as methyl or ethyl ester.

Alginate is a polysaccharide containing homopolymeric blocks of (1-4)-linked β-D-mannuronate and α-L-guluronate (G) residues, respectively, covalently linked together in different sequences or blocks. Alginate can be present in form of its salts, such as alkaline metal or earth alkaline metal salts, or in esterified form, such as in form of an alkyl ester, preferably methyl ester. Alginate is able to quickly absorb water to form a hydrogel. Thus, alginate can be used as gelling agent.

Chitosan is a linear biopolymer (polysaccharide) containing randomly distributed β-(1,4)-linked D-glucosamine units (deacetylated unit) and N-acetyl-D-glucosamine units, wherein the polymeric chain preferably contains more D-glucosamine units than N-acetyl-D-glucosamine units. Chitosan can be obtained from chitin by deacetylation either enzymatically or via an alkaline compound such as sodium hydroxide.

Hyaluronic acid is an important component of the connective tissue. Hyaluronic acid is a polymer which contains a disaccharide as repeating unit, wherein the chain comprises 250 to 50.000 of the disaccharide units. Said disaccharide comprises D-glucuronic acid and N-acetyl-D glucosamine being bound via a glycosidic β-(1,3) linkage. Hyaluronic acid can be present in form of its salts, such as alkaline metal or earth alkaline metal salts, in particular in the form of the sodium or potassium salt.

Gellan (also referred to as gellan gum) is an anionic polysaccharide obtained via fermentation of carbon hydrates by a bacterium called *Pseudomonas elodea*. Gellan is a polymer containing a tetrasaccharide as repeating unit, wherein the chain comprises 250 to 50.000 of the tetrasaccharide units. Said tetrasaccharide units comprise two residues of D-glucose, one residue of L-rhamnose and a residue of D-glucuronic acid in the following order: D-glucose-D-glucuronic acid-D-glucose-L-rhamnose. A part of the D-glucose residues can be esterified with acetic acid and/or glycerol acid. Further, the D-glucuronic acid residues can be present in form of a salt, preferably in form of the potassium, sodium, magnesium and calcium salt.

A polypeptide is a chain of amino acids linked together, wherein a single polypeptide chain might make up the entire primary structure of a simple protein. More complex proteins are formed when two or more polypeptides are linked together. Polypeptides can be naturally occurring or obtained via peptide synthesis for example via Merrifield Synthesis.

A cellulose-based hydrogel is a hydrogel based on cellulose and/or its derivatives. Cellulose is a polysaccharide containing a linear chain of several hundred to many thousands of β(1→4)-linked D-glucose units. Within the present application cellulose derivatives are for example cellulose ether and cellulose ester as well as their salts. Examples of cellulose ethers are hydroxyalkyl cellulose, in particular hydroxy $C_{1-6}$-alkyl cellulose such as hydroxymethyl cellulose, hydroxyethyl cellulose, hydroxypropyl cellulose, hydroxyisopropyl cellulose and hydroxybutyl cellulose, preferably hydroxymethyl cellulose and/or hydroxyethyl cellulose. Examples of cellulose esters are carboxyalkyl cellulose, in particular carboxy $C_{1-6}$-alkyl cellulose, such as carboxymethyl cellulose, carboxy ethyl cellulose, carboxypropyl cellulose, carboxybutyl cellulose and/or their salts. Preferred are carboxymethyl cellulose and carboxy ethyl cellulose and their salts, in particular the sodium salt. Further, a mixture of the mentioned compounds can be used. The number average molecular weight of cellulose and/or its derivates is 1.000 g/mol to 250.000 g/mol, preferably 5.000 g/mol to 175.000 g/mol, in particular 10.000 g/mol to 100.000 g/mol, determined with gel permeations chromatography.

The selected hydrogel comprised by the present composition can be preferably based on synthetic polymeric material selected from polyvinyl alcohol, polyalkylene oxide-based hydrogel, poly(meth)acrylate-based hydrogel, poly (eth)-acrylate-based hydrogel, poly alkyl(meth)acrylate-based hydrogel, poly alkyl(meth)acrylate-based hydrogel, vinyl polymer based hydrogel, polycaprolactam- and poly-caprolactone-based hydrogel, polyurethane-based hydrogel, poly-urea-based hydrogel and polyurethane-polyurea-copolymer-based hydrogel.

In a preferred embodiment the synthetic polymeric material has a number average weight of 2.500 to 250.000.000 g/mol, preferably 5.000 to 5.000.000 g/mol, in particular 50.000 to 1.000.000 g/mol.

Polyalkylene oxide is a compound which can be represented by the formula H—(O-A)$_n$-OH, wherein A is an alkylene group, preferably a linear alkylene group comprising 2 to 6 carbon atoms, in particular 2 or 3 carbon atoms. Preferred polyalkylene oxides are polyethylene oxide (also referred to as polyethylene glycol), polypropylene oxide (also referred to as polypropylene glycol) and a copolymer from polyethylene oxide and polypropylene oxide.

Poly(meth)acrylate and poly(eth)acrylate are polymers obtained by polymerisation of the corresponding acid, i.e. (meth)acrylic and eth(acrylic) acid, respectively. Polyalkyl (meth)acrylate and polyalkyl(eth)acrylate are alkylesters, preferably alkylesters with 1 to 6 carbon atoms, in particular methyl or ethyl ester of the before-mentioned (meth)acrylic and eth(acrylic) acids, respectively.

Vinyl polymer is a polymer derived from compounds containing a vinyl group, wherein the vinyl group can be substituted or unsubstituted, preferably substituted. Substituents can be aromatic groups, such as benzene, alkyl groups, preferably $C_1$ to $C_6$ alkyl groups, or other substituents, such as halogens, hydroxy and nitrile. Particularly preferred is polyvinyl alcohol. Polyvinyl alcohol is a hydrophilic polymer which can be represented by the formula —(CH$_2$CHOH)n-. For example polyvinyl alcohol having a molecular weight of about 130.000 Daltons can be used to form a hydrogel for example by dissolving polyvinyl alcohol in water and freezing and thawing said mixture.

Polycaprolactam and polycaprolactone are the polymers of the corresponding caprolactam and caprolactone. Caprolactam and caprolactone can be substituted, for example with the substituents as mentioned above, or unsubstituted, preferably unsubstituted.

Polyurea is a polymer represented by the following formula

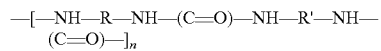

wherein R and R' are aliphatic or aromatic residues.

Polyurethane (PUR and PU) is a polymer composed of organic units joined by urethane (carbamate) links. Polyurethane is represented by the following formula

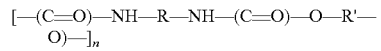

wherein R and R' are aliphatic or aromatic residues.

In a particularly preferred embodiment of the invention the selected hydrogel comprised by the present composition is a hydrogel based on a polyurethane-polyurea-copolymer. The polyurethane-polyurea-copolymer can be preferably obtained by reacting a mixture comprising a prepolymer having at least two isocyanate end groups, a diamine and a polyhydric alcohol.

It is preferred that the prepolymer having at least two isocyanate end groups has two to four isocyanate end groups, in particular two isocyanate end groups. It is further preferred that the prepolymer having at least two isocyanate end groups is an aliphatic prepolymer having at least two isocyanate end groups. In a particularly preferred embodiment the prepolymer having at least two isocyanate end groups is a prepolymer having two isophoroneisocyanate end groups. The prepolymer having at least two isophoroneisocyanate end groups can preferably be present in the mixture in an amount of 5 to 20 wt. %, preferably 6 to 18 wt. %, in particular 8 to 16 wt. %, based on the total weight of the mixture.

The diamine comprised in the mixture can preferably be an aliphatic diamine. It is more preferred that the diamine is an alkylene oxide-based diamine. An alkylene oxide-based diamine is an alkylene oxide whose hydroxy end groups are substituted by amine groups. An alkylene oxide-based diamine can also be referred to as polyether amine. It is preferred that alkylene is alkylene having 1 to 6 carbon atoms, preferably 1 to 4 carbon atoms. Particularly preferred are methylene, ethylene, propylene and mixtures thereof, especially a mixture of ethylene and propylene. Diamine can preferably be present in the mixture in an amount of 5 to 70 wt. %, provided that the ratio of the isocyanote groups (of the prepolymer) to amino groups (of the diamine) is 1.15 to 1.45, preferably 1.20 to 1.40, in particular 1.25 to 1.35, based on the total weight of the mixture.

A polyhydric alcohol preferably comprises diols, triols, tetrols, pentols and hexols and mixtures thereof, more preferably diols, triol, hexols and mixtures thereof. In particular the polyhydric alcohol can be selected from glycols, especially ethylene glycol and propylene glycol, sorbitol and glycerol and mixtures thereof. The polyhydric alcohol can preferably be present in the mixture in an amount of 5 to 50 wt. %, preferably 10 to 45 wt. %, in particular 15 to 40 wt. %, based on the total weight of the mixture. Polyhydric alcohols are excellent moisturizing agents and, thus, provide a nourishing component for the skin surrounding the wound.

Further, the mixture can preferably comprise an inorganic salt. The inorganic salt comprises preferably an inorganic halide, in particular chloride. Further, the inorganic salt is an alkali metal or earth alkali metal salt. Examples are sodium chloride, potassium chloride, magnesium chloride and calcium chloride. In a particularly preferred embodiment the inorganic salt is sodium chloride. The inorganic salt can preferably be present in the mixture in an amount of 0 to 5 wt. %, more preferably 0.5 to 3 wt. %, in particular about 1 wt. % based on the total weight of the mixture.

As described above, the polymeric material can be regarded as a matrix or a hydrogel matrix, in particular a dry hydrogel matrix. The presently selected hydrogel matrixes can absorb water and are thus subsequently regarded as specifically selected polymeric material-based hydrogels. The corresponding hydrogels are especially suitable to store water and then to deliver it to the wound to maintain the wound humid.

In a preferred embodiment the present hydrogel contains at least 20 wt. %, preferably at least 30 wt. %, more preferably at least 40 wt. %, in particular at least 50 wt. % of water, wherein the hydrogel preferably contains at most 90 wt. %, more preferably at most 80 wt. % of water. Thus, a wound system can be provided that on the one hand is able to provide water to maintain the wound sufficiently humid for a natural wound healing and on the other hand is able to absorb undesired fluid, such as exudate from the wound.

In line with the present invention the amount of water contained in the hydrogel should be verified via DIN EN 14079, wherein the amount of water is calculated as follows:

$$W_w = \frac{W_g - W_t}{W_g} \cdot 100\% \quad (1)$$

wherein
$W_w$=weight of water in %, based on the total weight of the hydrogel,
$W_g$=weight of the hydrogel
$W_t$=weight of the "dry component" of the hydrogel (corresponding to the hydrogel matrix).

In the context of the invention the amount of water should be considered as water that can be theoretically released from the hydrogel. Contrary, water that is covalently bound should not be considered as belonging to the above-mentioned amount of water.

In a more preferred embodiment of the invention the hydrogel is a polyurethane-based hydrogel, more preferably a polyurethane-polyurea-copolymer-based hydrogel. In a preferred embodiment the hydrogel can comprise at least 20 wt. % of water and at least 10 wt. % of polyurethane-polyurea-copolymer. An alternative hydrogel comprises at least 20 wt. % of water and at least 15 wt. % of polyurethane-polyurea-copolymer.

Further, it is preferred that the polymeric syntactic material (hydrogel matrix) is formed from 6 to 60 wt. % of a prepolymer with aliphatic diisocyanate groups, 4 to 40 wt. % polyamine on a polyethylene oxide basis, at least one salt selected from sodium chloride, potassium chloride, magnesium chloride, calcium chloride or mixtures thereof and at least 20 wt. % of water.

Alternatively, it is preferred that the polymeric synthetic material (hydrogel matrix) is formed from 6 to 30 wt. % of a prepolymer with aliphatic diisocyanate end groups, 4 to 20 wt. % polyamine on a polyethylene oxide basis, at least one salt selected from sodium chloride, potassium chloride, magnesium chloride, calcium chloride or mixtures thereof and at least 30 wt. % of water.

Particularly it is preferred that the polymeric synthetic material (hydrogel matrix) is formed from 6 to 20 wt. % of a prepolymer with two isophoronecyanate end groups, 4 to 15 wt. % of diamine on a polyethylene oxide basis, 0.5 to 15 wt. % of a salt selected from sodium chloride, potassium chloride, magnesium chloride, calcium chloride or mixtures thereof and at least 40 wt. % water.

In a preferred embodiment the hydrogel layer has a thickness of 0.1 to 5.0 mm, more preferably 0.3 to 4.0 mm, in particular 0.5 to 3.0 mm.

The present wound dressing comprises a layer comprising a pH-sensitive polymer,

For the purposes of the present invention, a pH-sensitive polymer is a substance or mixture of substances composed of a multiplicity of repeating monomer units, having a first solubility or dissolution rate in an aqueous solution at a defined temperature and a first pH, and, at the same temperature and at a second pH, which is different from the first pH, having a second solubility or dissolution rate, which is different from the first solubility or dissolution rate. This results in different solubilities or dissolution rates of the polymer at different pH values. In a preferred embodiment the solubility of the pH-sensitive polymer at a pH value of 4 is less than at a pH value of 8. Thus, such a pH-sensitive polymer can be regarded as a barrier against acidic aqueous solution, while alkaline aqueous solution can at least partially dissolve said pH-sensitive polymer and thus pass the barrier.

Suitable pH-sensitive polymers are those which at a pH of less than 6.0 in aqueous solution are not soluble, i.e. the solubility is less than 0.5% (w/w), preferably less than 0.2% (w/w), in particular less than 0.1% (w/w) and at a pH of more than 7.0 are soluble in an amount of at least 1% (w/w), preferably at least 1.5% (w/w), in particular at least 2.5%

(w/w). Preferred are pH-sensitive polymers, wherein the dissolution rate of the pH-sensitive polymer at 20° C. in an aqueous solution at a pH of 6 is less than 0.1 mg/min/g, i.e. less than 0.1 mg/min per gram of the pH-sensitive polymer are dissolved in the aqueous solution at a pH of 6. It is further preferred that the dissolution rate of the pH-sensitive polymer in an aqueous solution at a pH of 8.0 in aqueous solution at 20° C. is more than 1 mg/min/g, preferably more than 10 mg/min/g.

Suitable polymers for the use as pH-sensitive polymers are cellulose acetate phthalate, cellulose acetate trimellitate, hydroxypropyl methylcellulose acetate succinate, carboxymethylethyl cellulose, oxidized regenerated cellulose, poly-acrylates and copolymers and mixtures thereof. Preferred polymers include copolymers of (meth)acrylic acid with alkyl (meth)acrylate, wherein alkyl is methyl, ethyl or butyl.

In a preferred embodiment the pH-sensitive polymer can be a poly ((meth)acrylic acid-co-alkyl (meth)acrylate), preferably in a ratio of 2:1 to 1:3.

A preferred pH-sensitive polymer is poly(methacrylic acid-co-methyl acrylate) in a ratio of about 1:1. An alternatively preferred pH-sensitive polymer is (methacrylic acid-co-methyl acrylate) in a ratio of about 1:2.

In an alternatively preferred embodiment the pH-sensitive polymer can be a poly(methyl acrylate-co-methyl methacrylate-co-methacrylic acid), preferably in a ratio of about 7:3:1.

In a preferred embodiment the layer comprising a pH-sensitive polymer further comprises a plasticizer.

Within the present application a plasticizer can be regarded as a substance that is added to a polymer to alter the physical properties of said polymer. In particular, a plasticizer can be a solid substance that increases the plasticity or decreases the viscosity of a polymeric material by decreasing the attraction between polymer chains to enhance their flexibility. Examples of plasticizers for polymeric material can be organic substances, such as phthalate esters or oligomers, polymers of different polymeric chains than the ones of the polymer that should be plasticized/softened.

An example of such an oligomer/polymer suitable as plasticizer is polyethylene glycol having a molecular weight from 400 to 12000 g/mol, preferably from 1500 to 10000 g/mol, in particular from 7300 to 9000 g/mol.

Layer b) preferably comprises pH-sensitive polymer and plasticizer in a weight ratio of 3:1 to 12:1, more preferably of 4:1 to 9:1, in particular 5:1 to 7:1, especially about 6:1.

Further the present wound dressing comprises one or more compartments comprising carrier containing fluorescent dye, wherein each compartment is placed in or on layer b) comprising a pH-sensitive polymer.

Within the present application a compartment is regarded as a three-dimensional shape with distinct boundary surfaces such that the compartment can be clearly distinguished from its surroundings. The compartment can preferably be a three-dimensional shape of any kind, such as a disc-like, pellet-like, spherical, cubic, cuboid, ovoid, droplet-like, teardrop-like, tetrahedron-like and octahedron-like.

In the present application each compartment is placed in or on layer b) comprising a pH-sensitive polymer.

A compartment placed in layer b) is regarded as being completely surrounded by said layer, i.e. all the boundary surfaces of the compartment are between the compartment and layer b).

A compartment placed on layer b) is regarded as being embedded or partially embedded in said layer, i.e. at least one of the surfaces of the compartment is not between the compartment and layer b).

A carrier can be regarded as a medium or a component to be comprised by the compartment. Thus, the carrier can be regarded to fill, preferably completely fill, the compartment. In addition, the carrier contains a fluorescent dye, wherein said carrier ensures that said fluorescent dye is not released until in contact with aqueous substances. It is further preferred that, as long as the dye is completely contained in the carrier, no coloration of the dye upon excitation with the corresponding excitation wavelength of the dye can be detected when inspecting the wound dressing.

The carrier can preferably be of the same material as the one comprised by layer a) or b).

In a preferred embodiment of the present invention the carrier can be the same pH-sensitive polymer comprised in layer b). In case that the carrier is the same pH-sensitive polymer as in layer b), due to the presence of fluorescent dye contained in the carrier the compartment can be nevertheless clearly distinguished from layer b).

In an alternative embodiment the carrier can be a hydrogel as described above with regard to layer a).

In a more preferred embodiment of the present invention the carrier can be a hydrogel, wherein the hydrogel comprised by the present composition can be preferably based on synthetic polymeric material. Preferred is a hydrogel based on polyalkylene oxide-based hydrogel, such as polyethylene glycol-based hydrogel, polypropylene glycol-based hydrogel, polyethylene glycol/polypropylene glycol-based hydrogel, polyvinyl alcohol-based hydrogel, vinyl polymer-based hydrogel, such as polyvinylpyrrolidone, methylcellulose-based hydrogel, hydroxypropyl methylcellulose-based hydrogel, polycaprolactam- and polycaprolactone-based hydrogel, polyurethane-based hydrogel, polyurea-based hydrogel and poly-urethane-polyurea-copolymer-based hydrogel.

Preferred is polyvinyl alcohol-based hydrogel. Alternatively preferred is hydrogel based on a polyurethane-polyurea-copolymer as described with regard to layer a).

As indicated above the wound dressing according to the present invention comprises a carrier containing a fluorescent dye.

A fluorescent dye is a fluorescent chemical compound able to re-emit light upon excitation. It is particularly preferred that the fluorescent dye is excited with a wavelength in the UV range, preferably 100 to 380 nm, more preferably 200 to 300 nm, in particular about 250 nm, especially 254 nm. It is further preferred that the re-emitted light has a wavelength in the visible range, preferably from 400 to 750 nm, more preferably from 500 to 600 nm, in particular about 520 nm, especially 517 nm.

Fluorescent dyes are often grouped into classes, such as acridine dyes, cyanine dyes, fluorone dyes, oxazine dyes, phenanthridine dyes and rhodamine dyes. Preferred are fluorone dyes.

In a preferred embodiment of the invention the fluorescent dye belongs to the group of xanthenes bearing at least one hydroxy group at the xanthene skeleton. Fluorescent dyes based on a xanthene system bearing at least one hydroxy group at the xanthene skeleton are for example eosins such as eosin B and eosin Y and fluorescein dyes such as 6-carboxyfluorescein (also referred to as carboxyfluorescein), 2,7-dichlorofluorescein and fluorescein.

In a particularly preferred embodiment the fluorescent dye is fluorescein or carboxyfluorescein, especially carboxyfluorescein.

In a preferred embodiment the fluorescent dye is contained in an amount of 0.1 µg/cm² wound dressing to 100 mg/cm² wound dressing, preferably 1 µg/cm² wound dressing to 50 mg/cm² wound dressing, in particular 10 µg/cm² wound dressing to 10 mg/cm² wound dressing.

In a preferred embodiment carboxyfluorescein is contained in the wound dressing in an amount of 100 µg/cm² wound dressing to 100 mg/cm² wound dressing, preferably 1 mg/cm² wound dressing to 50 mg/cm² wound dressing, in particular 3 mg/cm² wound dressing to 8 mg/cm² wound dressing.

In a preferred embodiment the carrier can further contain an inorganic salt and or a buffer.

An inorganic salt is preferably a salt with a metal ion, preferably an alkaline or earth alkaline metal ion, as cation and an anion selected from phosphate, sulfate, nitrate and halogen, preferably halogen.

In a preferred embodiment the carrier further contains a buffer.

Within this application compositions which include both Brønsted acid and corresponding base can be regarded as a buffer (also referred to as buffer substances). A Brønsted acid is a substance which in reaction with suitable solvents, usually water, is able to give up hydrogen cations (protons). Products of this reaction are a protonated solvent particle and a so-called acid residue, which represents the corresponding or conjugate base to the Brønsted acid.

A feature of these compositions is that in aqueous solution they stabilise the pH of the solution, even if quantities of an acid or of a base are added to the aqueous solution. An acid added to the aqueous solution reacts with the base present in the buffer substance to form a new particle of the Brønsted acid corresponding to the base. No further hydroxonium or hydroxide ions are produced, and so the pH remains virtually unchanged. This pH stabilisation operates for as long as the quantity of base or acid particles present does not become excessive. The quantitative extent of this stabilisation is referred to as the buffer capacity.

If a Brønsted acid is used together with its corresponding base as buffer substance, the molar ratio of Brønsted acid to its corresponding base is 100:1 to 1:100, preferably 10:1 to 1:10, more preferably 1:1. An equimolar mixture of Brønsted acid and its corresponding base possesses the greatest pH stability to addition of acid or base.

In one preferred embodiment the Brønsted acid and additionally a substance which represents a Brønsted base corresponding to the Brønsted acid are contained in the carrier.

Brønsted acids employed with preference are those selected from acetic acid, citric acid, lactic acid, glyceric acid, gluconic acid, benzoic acid, aconitic acid, glutaric acid, tartaric acid, phosphoric acid, maleic acid, succinic acid and glutamic acid. These Brønsted acids have an advantageous $pK_a$ of between 2 and 5, are physiologically unobjectionable and can be used in wound healing.

In a preferred embodiment of the present invention, after being dissolved in demineralised water at 37° C. the buffer substances form a buffer solution with a pH value ranging between 3 and 7, preferably between 3.2 and 6.5, more preferably between 3.4 and 5.5 and especially preferably between 3.6 and 5.0. It was found out that in the above-indicated pH range a particularly favourable wound healing as well as suppression of fibrin formation and/or fibrin mesh can be achieved. It was also found that the suppression of scar tissue is particularly favourable in this pH range.

For the wound dressing of the present invention, the pH value that results when the buffer substances forming the buffer solution are dissolved is determined with a pH measurement. For such a measurement, the buffer substances are completely dissolved under stirring in a concentration of 0.1 M in one litre of demineralised water having a temperature of 37° C., thus forming the buffer solution. The pH of the buffer solution can be measured with the generally known method with a common potentiometry-based pH meter. It is preferred that the apparatus Labor-Daten-pH-Meter CG841 by Schott Geräte GmbH with a glass electrode FlushTrode by Hamilton Messtechnik GmbH is used. The pH meter should be calibrated before measuring using commercially available calibration solutions and be used in accordance with the manufacturer's instruction manual. The pH of the buffer solution is measured by dipping the measuring electrode of the pH meter into the buffer solution while stirring the buffer solution. Such a buffer solution can be used to stabilise the pH value of a liquid within a certain pH range, wherein this pH range is also referred to in the present context as the buffer range. The above-indicated liquid may be wound exudate Particularly preferred for use as Brønsted acid are citric acid, benzoic acid and/or lactic acid, optionally together with their corresponding bases. Alternatively, in a particularly preferred embodiment the buffer substances are selected from benzoic acid/benzoate, citric acid/citrate and lactic acid/lactate. The tissue compatibility of these Brønsted acids is particularly good.

When contained in a carrier comprised by a compartment, Brønsted acids are present in amounts of 0.01-100 mmol of Brønsted acid, preferably 0.1-10 mmol of Brønsted acid, more preferably 0.2-5 mmol of Brønsted acid per gram of the wound dressing. One or more Brønsted acids, optionally together with their corresponding bases, may also be present in the hydrogel layer a) and or in an optional backing layer. It has emerged that such an amount of Brønsted acid allows the pH of the wound exudate to be influenced in a particularly advantageous way.

In an alternative preferred embodiment, the buffer (substance) is based on an alkaline organic compound, more preferably the buffer comprises a 4-(2-hydroxyethyl)-1-piperazinethane sulfonic acid. 4-(2-hydroxyethyl)-1-piperazin-ethane sulfonic acid is represented by the following chemical formula:

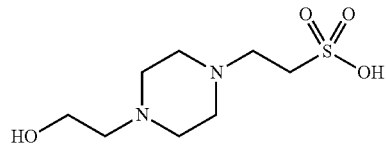 [SMILES: O=S(=O)(O)CCN1CCN(CCO)CC1]

When contained in a carrier comprised by a compartment 4-(2-hydroxyethyl)-1-piperazineethane sulfonic acid is present in an amount of 0.01-100 mmol, preferably 0.1-10 mmol, more preferably 0.2-5 mmol.

In a preferred embodiment the carrier further contains one or more therapeutic substance(s).

A therapeutic substance can be referred to as a substance for treating or curing a disease, preferably by achieving a healing effect.

Examples of therapeutic substances are antimicrobial substances such as antiseptics, antimicrobial metals and antibiotics, anti-inflammatory and/or analgesic substances such as nonsteroidal anti-inflammatory drugs, growth factors, antibiofilm substances such as antimicrobial peptides (also referred to as AMPs), enzymatic substances such as trypsin, protease inhibitors such as tissue inhibitor of metalloproteinases (also referred to as TIMPs), and mixtures thereof.

Examples of nonsteroidal anti-inflammatory drugs (also referred to as NSAIDs) include acetylsalicylic acid, diclofenac, ibuprofen, indomethacin, metamizole and paracetamol.

Examples of growth factors include epidermal growth factor (EGF) fibroblast growth factor (FGF), insulin-like growth factor (IGF), keratinocyte growth factor (KGF), platelet-derived growth factor (PDGF), transforming growth factor (TGF) or vascular endothelial growth factor (VEGF).

Preferred are antimicrobial substances as therapeutic substance.

An antimicrobial substance is an agent intended to reduce the presence of microorganisms such as bacteria by killing them or at least preventing their population from growing. Classes of antimicrobial substance are for example disinfectants, antimicrobial metals, antiseptics and antibiotics.

Examples of antimicrobial substances are benzalkonium chloride, chlorhexidine, iodine, polyvidone-iodine, octenidine, polyhexanide (PHMB), silver and its salts, preferably in nanoparticular form, zinc oxide, preferably in nanoparticular form, beta-lactam antibiotics such as benzylpenicillin, phenoxymethylpenicillin, oxacillin, ampicillin, amoxicillin, cefotaxime, ceftriaxone and cefepime, minoglycoside antibiotics such streptomycin, gentamicin, kanamycin and neomycin, tetracycline antibiotics such as tetracycline, oxytetracycline, doxycycline and minocycline, macrolide antibiotics such as erythromycin, clarithromycin, roxithromycin, azithromycin, spiramycin, quinolone antibiotics such norfloxacin, ciprofloxacin, ofloxacin, levofloxacin, sparfloxacin and moxifloxacin, antimicrobial peptides (AMPs) such as pexiganan, iseganan and omiganan, and mixtures thereof.

In a more preferred embodiment the one or more therapeutic substance is an antibiotic, more preferably a quinolone antibiotic.

In a particular preferred embodiment the one or more therapeutic substance(s) is norfloxacin, ciprofloxacin, ofloxacin, levofloxacin, sparfloxacin and/or moxifloxacin, especially ciprofloxacin.

In preferred embodiment the carrier contains a buffer and/or one or more therapeutic substance(s).

In a preferred embodiment of the invention layer b) and carrier containing fluorescent dye and being comprised by layer b) are in direct contact with each other, i.e. there are no further layers between them.

Further, layer b) preferably comprises one or more recesses in the side opposite the wound, preferably in the surfaces opposite the wound, wherein in said one or more recesses the one or more compartments c) are embedded.

In one embodiment, the compartment comprising carrier containing fluorescent dye is preferably placed on layer b) comprising pH-sensitive polymer. In a more preferred embodiment layer b) preferably comprises one or more recesses opposite the wound, preferably in the side opposite the wound, wherein each compartment is embedded in said recesses. Thus, compartments c) comprising carrier containing fluorescent dye is/are embedded in layer b). As indicated embedded can be referred to as being partially surrounded by layer b). For example, layer b) can be provided with recesses, such as holes, in which the carrier containing fluorescent dye can be filled or incorporated.

Further, the wound dressing preferably comprises a backing layer d).

This backing layer d) can consist of various materials. Typically, wound dressings utilize textile backing materials, nonwovens, polymer films or polymer foams.

This backing layer may be in direct or indirect contact with the layer comprising a pH-sensitive polymer.

The backing layer of a wound dressing that is in accordance with the present invention may utilize in particular polymer films or polyurethane foams. Very particular preference is given to polymer films or polymer foams which are water impermeable and have a high moisture vapor permeability. Films or foams particularly suitable for this are fabricated from polyurethane, polyether urethane, polyester urethane, polyether-polyamide copolymers, polyacrylate or polymath-acrylate. More particularly, a water impermeable and moisture vapor permeable polyurethane film or a water impermeable and moisture vapor permeable polyurethane foam is suitable for use as backing layer d). More particularly, a polyurethane film, polyester urethane film or polyether urethane film is preferable for use as polymer film. However, very particular preference is also given to polymer films from 15 to 50 μm, more particularly from 20 to 40 μm and most preferably from 25 to 30 μm in thickness. The moisture vapor transmission rate of the polymer film of the wound dressing is preferably at least 750 g/m$^2$/24 h, more particularly at least 1000 g/m$^2$/24 h and most preferably at least 2000 g m$^2$/24 h (measured to DIN EN 13726). In particularly preferred embodiments, these films have a moisture-proof tacky edge portion. This edge portion ensures that the wound dressing can be applied to and fixed at its intended location. It is further ensured that liquid cannot escape between the film and the skin surrounding the area to be treated. Particularly preferable adhesives achieve in a thin add-on of 20 to 35 g/m$^2$ a moisture vapor transmission rate combined with the film of at least 800 g/m$^2$/24 h and preferably of at least 1000 g/m$^2$/24 h (measured to DIN EN 13726).

In a preferred embodiment of the invention the present wound dressing comprises
  a) a hydrogel layer facing towards the wound,
  b) a layer comprising a pH-sensitive polymer, and
  c) one or more compartment(s) comprising carrier containing fluorescent dye,
  d) a backing layer,
wherein each compartment c) is placed in or on layer b).

It is further preferred that layer b) and one or more compartments comprising carrier containing fluorescent dye is arranged between hydrogel layer a) and backing layer d) such that the surface of layer b) in which each compartment is embedded is directed to the backing layer.

In a preferred embodiment two neighbouring layers comprised by the present wound dressing are adhered to each other. To be adhered can be regarded as being bonded for example chemically bonded to each other so that the layers are not horizontally movable against each other.

A further subject of the invention is a method for preparing a layer comprising a pH-sensitive polymer and one or more compartment(s) comprising carrier containing fluorescent dye, wherein the one or more compartment(s) is/are embedded in a pH-sensitive polymer, comprising the steps of
  (i) providing a layer comprising a pH-sensitive polymer and having recesses, (ii) adding a solution comprising precursor carrier and fluorescent dye into the recesses, and (iii) hardening the carrier.

In step (i) a solution, preferably a complete solution, of pH-sensitive polymer in a solvent is prepared. The solution preferably further contains a plasticizer. As far as the pH-sensitive polymer and the plasticizer are concerned, the same applies as described above with regard to the wound dressing. Suitable solvents are for example water or alcohol with 1 to 4 carbon atoms or a mixture thereof. Preferred are ethanol, water or a mixture thereof, in particular water.

The solution is transferred into a mould, preferably a mould having wells or recesses. Subsequently the solution is dried at an elevated temperature to remove the solvent a least partially.

An elevated temperature is referred to as a temperature being higher than room temperature corresponding to 23° C. and lower than the boiling temperature of the solvent. When water is used as solvent, an elevated temperature is preferably 40° to 80° C., in particular about 50° C.

Drying is conducted for 6 to 90 hours, preferably for 18 to 85 hours, in particular 48 to 72 hours.

After drying, a hardened layer containing pH-sensitive polymer and having recesses is removed from the mould.

In step (ii) a solution comprising carrier or a precursor of carrier and fluorescent dye is added into the recesses of the layer of step (i).

A precursor carrier can be regarded as a precursor of the carrier, wherein the precursor carrier, when hardened and/or crosslinked, is converted into the carrier itself.

The solvent for the solution comprising carrier or a precursor of carrier and fluorescent dye is preferably water or an alcohol with 1 to 4 carbon atoms, preferably ethanol, water or mixtures thereof. Particularly preferred is water as solvent.

In a preferred embodiment of step (ii) a solution containing fluorescent dye is prepared. As far as the fluorescent dye is concerned, the same applies as described above. In a preferred embodiment the solution comprises ciprofloxacin in a concentration of 10 mg/ml to 2.5 g/ml, preferably 50 mg/ml to 1 g/ml, in particular about 200 mg/ml. The solution can preferably further comprise an inorganic salt as described above with regard to the hydrogel, preferably sodium chloride and/or a buffer substance as described above, preferably 2-[4-(2-hydroxyethyl)piperazin-1-yl]ethanesulfonic acid. The pH of the solution is preferably adjusted to be less than 6, in particular about 5.5, achieved for example by the addition of an acid, preferably 0.1 N hydrochloric acid. The solution is preferably heated to an elevated temperature as described above, in particular to about 90° C.

Further, the precursor carrier or carrier is added to the solution containing fluorescent dye to obtain a solution comprising precursor carrier or carrier and fluorescent dye. This solution is filled into the recesses of the layer obtained in step (i) for example by spraying or pipetting.

In step (iii) the solution comprising precursor carrier or carrier and fluorescent dye as prepared in step (ii) is hardened and/or crosslinked. Step (iii) can for example be carried out by cryogenic hardening and/or crosslinking at temperatures from −30 to −10° C., preferably −25 to −15° C., in particular about −15° C.

The duration of step (iii) is preferably between 2 and 48 hours, more preferably between 12 and 30 ours, in particular about 30 hours.

A further subject of the present invention is a method for preparing a wound dressing according to the invention, wherein the method comprises the steps of (I) providing layer a) according to the present invention (II) applying layer b) and one or more compartments comprising carrier containing fluorescent dye, wherein each compartment is embedded in layer b) on layer a), wherein the compartment is embedded in the surface of layer b) being opposite to the surface being in contact with layer a)

(III) optionally applying a backing layer d) on the surface of layer b) wherein each compartment is embedded.

In step (I) a hydrogel layer is provided. As far as the hydrogel and its properties such as the contained water and thickness are concerned the same applies as described above.

In step (II) layer b) and one or more compartments comprising carrier containing fluorescent dye, wherein each compartment is embedded in layer b), is applied to layer a) such that each compartment embedded in the surface of layer b) being opposite to the surface being in contact with hydrogel layer a).

As far as layer b) and the compartments comprising carrier containing fluorescent dye and their arrangement in step (II) are concerned, the same applies as described above. In particular, the layer b) and the compartments comprising carrier containing fluorescent dye can be prepared as described above.

In optional step (III) a backing layer d) can be applied on the surface of layer b) wherein each compartment is embedded. As far as the backing layer is concerned the same applies as described above.

A further subject of the invention is the use of a compartment comprising carrier containing fluorescent dye, wherein said compartment is placed in or on a pH-sensitive polymer as infection indicator for wounds.

As far pH-sensitive polymer, compartment, carrier and fluorescent dye are concerned, the same applies as described above.

It turned out that the present compartment can be advantageously used as an indicator of the state of a wound, in particular as an indicator for an infection in a wound. In particular, in the presence of a wound healing normally without any disturbance, such as an infection, no fluorescent dye is released and no fluorescence can be detected. However, in case of for example a chronic or badly healing wound due to an infection, the present compartment releases fluorescent dye and the skilled person, such as a medic or doctor, is able to visually detect the fluorescence indicating the state of the wound and to act accordingly, for example by the administration of an antimicrobial agent.

Finally, a subject of the invention is a florescent dye for use in diagnosing an infection in a wound, wherein the fluorescent dye is contained in a carrier comprised by one or more compartments, wherein each compartment is placed in or on a layer comprising a pH-sensitive polymer.

As far as a pH-sensitive polymer, compartment, carrier and fluorescent dye are concerned, the same applies as described above.

Experimental Part

Analytical Methods:
Determination of the pH Value of the Hydrogel

To determine the pH value of the prepared hydrogels, a sample with a diameter of 35 mm was punched from the hydrogel and the starting weight of the sample was determined. Together with the fivefold amount of demineralized water the sample was transferred to a beaker and covered with a glass. The sample was incubated at 23° C. (room temperature) for 18 hours and after that period the hydrogel was removed from the sample and the pH value of the remaining liquid was determined in triplicate.

Determination of the Absorption Capacity of the Hydrogel

An important factor in modern wound treatment is creating and maintaining a moist wound environment while at the same time wound exudate is adsorbed and encapsulated in the wound dressing. For the characterization of the hydrogels regarding their absorption capacities, the amount of water uptake into the hydrogel is assessed at different points in time.

In this context, samples measuring 30 mm×30 mm are punched from the gels and their starting weight is determined. Then, the samples are put into beakers and covered with 120 ml demineralized water. The samples are stored at room temperature and taken out of the water at the different testing times (t=2 h, 4 h, 6 h, 8 h, 24 h, 30 h). Then they are put on a paper towel for five seconds per side to eliminate excess water before the gels are weighed.

Since the samples have different starting weights, the increase in weights [g] is considered for a better comparability. Each sample is examined in triplicate. The absorption capacity is calculated using the following formula:

$$W_A [g/g] = \frac{M_1 - M_0}{M_0}$$

$W_A$=water absorption capacity [g/g]
$M_0$=starting weight of the sample [g/g]
$M_1$=sample weight at time $t_x$ [g/g]

Determination of the Desorption Capacity of the Hydrogel

By maintaining a moist wound, the wound healing process is positively influenced. This is why one of the many requirements a wound dressing has to fulfil is the capacity to release moisture over an extended period of time.

This property is tested by measuring the desorption capacity of the hydrogels. For this test, samples measuring 30 mm×30 mm are punched from the gels and their starting weights are determined. Then, the samples are stored in a climate cabinet at a temperature of 32° C. and a relative humidity of 50% until each of the testing times. At the testing times (t=2 h, 4 h, 6 h, 8 h, 24 h, 30 h) the samples are taken from the climate cabinet and weighed again to determine weight loss or moisture loss over the time. The samples are examined in triplicate. Due to the different starting weights of the samples, the weight ratio of the samples at the different times is calculated using the following formula for a better comparability.

$$W_D [g/g] = \frac{M_1}{M_0}$$

$W_D$=water desorption capacity [g/g]
$M_0$=starting weight of the sample [g/g]
$M_1$=sample weight at time $t_x$ [g/g]

Preparation of the Wound Dressing

1. Hydrogel Layer

1.A For the preparation of the hydrogel two separate aqueous liquids A and B were prepared as follows.

Aqueous Liquid A:

Sodium chloride (6.24 g; 0.107 mol) was added to sterilized and demineralized water (990 ml) and stirred for five minutes at 23° C. to form solution 1. Solution 1 (767.5 g) and Jeffamine-Mix (50 wt. % Jeffamine and 50 wt. % water; 132.5 g) were mixed at 23° C. under stirring for five minutes to form aqueous liquid A (900 g).

Aqueous Liquid B:

Aqueous solution B is an aliphatic isocyanate prepolymer in water (isophorone diisocyanate in water, available under the name Aquapol from Carpenter; 900 g).

The preparation of the hydrogel was conducted by the pilot casting plant B100. Aqueous liquids A and B as prepared above were filled into the casting plant's two cartridges, respectively. To ensure an exact dosage and reproducibility the launch was started not before 12 hours after the filling of the cartridges. By doing this, inaccuracies for example due to bubbles can be prevented. The content of the cartridges was transferred via a pump through different tubes in a mixing chamber, wherein a ratio of aqueous liquid 2 to aqueous liquid 1 was adjusted to 1.5:1. In the mixing chamber the two components were stirred by a mixer and the reaction took place. The not completely polymerized hydrogel was released from the mixing chamber and subsequently cured completely. The pH of the gel was adjusted to a value of about 6.5 to 6.8 by washing with 0.1 M HCl.

Properties:

Adsorption capacity of the obtained hydrogel: see FIG. 1

Figure 2:
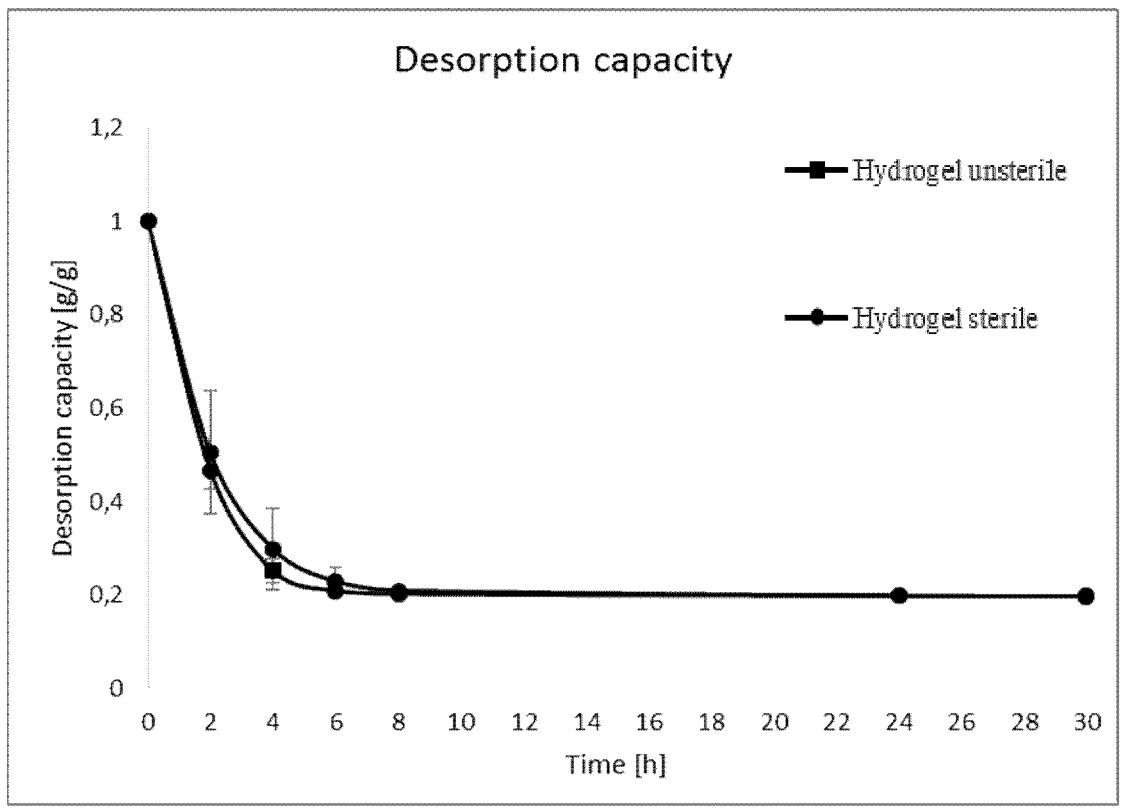
FIG. 2 shows a graph illustrating the desorption capacity of an obtained hydrogel of the present invention.

Desorption capacity of the obtained hydrogel: see FIG. 2

As can be seen from FIGS. 1 and 2, most water absorption as well as desorption occurs during the first eight hours, i.e. the present hydrogel is able to keep the wound moist as well as to adsorb wound exudate.

1.B An alternative hydrogel was prepared.

A solution comprising preferably 5%, poly(vinyl alcohol) (146 000-186 000 gmol$^{-1}$) in sterilized and demineralized water at 97° C. under constant magnetic stirring for 30 min was prepared. After cooling down and storing at −20° C. for at least 18 hours to promote cryogenic crosslinking a hydrogel based on PVA was obtained.

2. Layer Comprising pH-Sensitive Polymer, Wherein Compartments Comprising Carrier Containing Fluorescent Dye are Embedded 2.1 Preparation of Layer Comprising pH-Sensitive Polymer and Having Recesses 2.5 g polyethylene glycol having a molar weight of 7300 to 9000 g/mol were added under magnetic stirring at 700 rpm to 50 ml of a milky aqueous solution (dissolution) containing 30% poly(methyl acrylate-co-methyl methacrylate-co-methacrylic acid) in a ratio of about 7:3:1. Stirring was continued for twenty minutes followed by sonification for 5 minutes to aid in the removal of air bubbles. The obtained solution was poured into a silicone mould (59 Shore A silicone) and dried at 50° C. for 72 hours as indicated by the solution becoming colourless (see FIG. 3 A). After that the obtained layer comprising pH-sensitive polymer and having recesses (also referred to as wells) was separated from the mould (see FIG. 3 B).

2.2 Preparation of Solution Containing Carrier/Precursor Containing Fluorescent Dye 5-Carboxyfluorescin (9387 mg), sodium chloride (29.1 mg), 2-[4-(2-hydroxy-ethyl)piperazin-1-yl]ethanesulfonic acid (1192 mg), sodium hydroxide and 50 ml of deionised water were shaken and then sonicated until there were no visible particles. Subsequently the pH of the solution was adjusted with 1N hydrochloric acid to achieve a pH slightly below 6. The pH of the solution was measured using an electronic pH mater (Jenway, UK).

Polyvinyl alcohol (1 g) was added to 10 ml of the solution containing fluorescent dye. The solution was heated at 92° C. under magnetic stirring until polyvinyl alcohol particles were dissolved and a solution comprising precursor-carrier/carrier and fluorescent dye was obtained.

Figure 3:
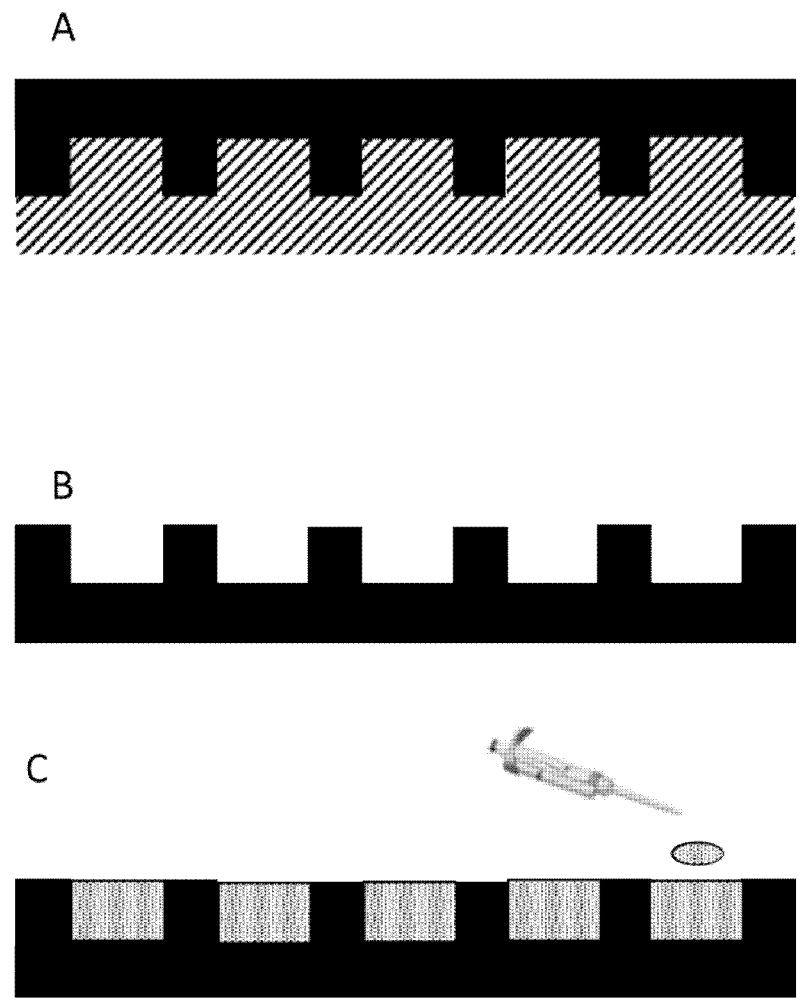
FIG. 3 illustrates the preparation of a hydrogel layer comprising a pH-sensitive polymer and having recesses in an embodiment of the present invention.

2.3 Layer Comprising pH-Sensitive Polymer Comprising Compartments Comprising Carrier Containing Fluorescent Dye 50 µl of the solution comprising precursor-carrier/carrier and fluorescent dye as prepared under item 2.2 was pipetted into each recess/well of the layer obtained from above item 2.1 (see FIG. 3 C). Subsequently the layer was placed at −20° C. for 24 hours to promote cryogenic crosslinking of PVA and to obtain a layer comprising pH-sensitive polymer comprising compartments comprising carrier containing fluorescent dye.

3. Wound Dressing

Figure 4:
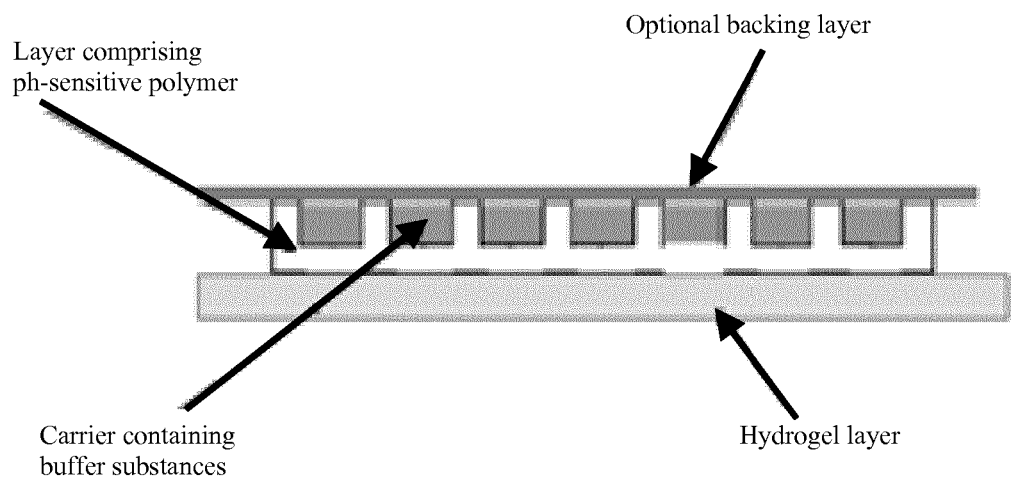
FIG. 4 illustrates a wound dressing having a hydrogel layer, a layer comprising a pH-sensitive polymer, and an optional backing.

To produce a wound dressing with the indicated properties the layers according to above items 1 and 2 were placed over one another, wherein the surface of the hydrogel layer not being in contact with the layer comprising the pH-sensitive polymer is foreseen to be directed to the wound. Further, the surface of the layer comprising pH-sensitive polymer, wherein the recesses were formed, is positioned opposite the wound and in contact with an optional backing layer (see FIG. 4). The dressing was sterilized with β-radiation using 25 kG.

The invention claimed is:

1. A wound dressing comprising:
   a) a hydrogel layer able to be orientated facing towards the wound,
   b) a layer comprising a pH-sensitive polymer, and
   c) one or more compartment(s) comprising carrier containing fluorescent dye,
   wherein each compartment c) is placed in layer b), and wherein layer b) comprises one or more recesses opposite the wound, wherein in said one or more recesses the one or more compartment(s) c) are embedded.

2. The wound dressing according to claim 1, wherein the hydrogel is a polyurethane-based hydrogel.

3. The wound dressing according to claim 1, wherein the solubility of the pH-sensitive polymer at a pH value of 4 is less than at a pH value of 8.

4. The wound dressing according to claim 1, wherein the solubility of the pH-sensitive polymer at 20° C. in an aqueous solution at a pH of 6 is less than 0.1 mg/min/g.

5. The wound dressing according to claim 4, wherein the solubility of the pH-sensitive polymer at 20° C. in an aqueous solution at a pH of 8 is more than 1 mg/min/g.

6. The wound dressing according to claim 1, wherein the solubility of the pH-sensitive polymer at 20° C. in an aqueous solution at a pH of 8 is more than 1 mg/min/g.

7. The wound dressing according to claim 1, wherein the pH-sensitive polymer is a (methyl acrylate-methyl methacrylate-methacrylic acid) copolymer.

8. The wound dressing according to claim 1, wherein layer b) further comprises a plasticizer.

9. The wound dressing according to claim 1, wherein the carrier is of the same material as the hydrogel or the pH-sensitive polymer.

10. The wound dressing according to claim 1, wherein the carrier is a polymer selected from polyethylene glycol, polypropylene glycol, polyethylene-polypropylene glycol copolymer, polyvinyl alcohol, polyvinylpyrrolidone, methylcellulose, hydroxypropyl methylcellulose and mixtures thereof.

11. The wound dressing according to claim 1, wherein the carrier is polyvinyl alcohol.

12. The wound dressing according to claim 1, wherein the fluorescent dye belongs to the group of xanthenes bearing at least one hydroxy group.

13. The wound dressing according to claim 1, wherein the fluorescent dye is fluorescein or carboxy fluorescein.

14. The wound dressing according to claim 1, wherein the carrier contains a buffer and/or one or more therapeutic substance(s).

15. A method of treating a wound comprising the step of applying a wound dressing to the wound, wherein said wound dressing comprises:
   a) a hydrogel layer able to be orientated facing towards the wound,
   b) a layer comprising a pH-sensitive polymer, and
   c) one or more compartments comprising a carrier containing fluorescent dye,
   wherein each of the one or more compartments c) is placed in layer b), wherein layer b) comprises one or more recesses opposite the wound, wherein in said one or more recesses the one or more compartments c) comprising the carrier containing fluorescent dye are embedded as an infection indicator.

* * * * *